United States Patent [19]

Decker, Jr. et al.

[11] Patent Number: 4,925,666
[45] Date of Patent: May 15, 1990

[54] SOLUBILIZED BENZOYL PEROXIDE AND COSMETIC SOLUTION INCLUDING SOLUBILIZED BENZOYL PEROXIDE

[76] Inventors: Donald F. Decker, Jr., 358 W. 46 St., Hialeah, Fla. 33012; Deborah A. Decker, 7425 SW. 12 Ct., North Lauderdale, Fla. 33068; Kathleen S. Duggins, 4059 Wimbledon Dr., #14, Cooper City, Fla. 33026

[21] Appl. No.: 301,625

[22] Filed: Jan. 25, 1989

Related U.S. Application Data

[63] Continuation of Ser. No. 16,839, Feb. 20, 1987, Pat. No. 4,857,302.

[51] Int. Cl.$^5$ ............................................. A61K 7/00
[52] U.S. Cl. .................................... 424/401; 424/78; 424/62
[58] Field of Search .................. 424/78, 62, 401, 59, 424/70

[56] References Cited

U.S. PATENT DOCUMENTS 4,478,853 10/1984 Chaussee ........................ 424/59 X Primary Examiner—Thurman K. Page
Attorney, Agent, or Firm—Robert C. Kain, Jr.

[57] ABSTRACT

The solubilized benzoyl peroxide is made by mixing a heated combination of crystalline benzoyl peroxide with silicone glycol copolymer wherein the temperature of the mixture is in the range from 45° to 65° C. The benzoyl peroxide is no longer in crystallized form and hence the benzoyl peroxide is solubilized in the silicone glycol copolymer. The cosmetic solution includes a solubilized benzoyl peroxide as described above. Further, an independent mixture of alcohol, acetone and water is made. The solubilized benzoyl peroxide is then mixed with the second mixture (alcohol, acetone and water). The resulting cosmetic solution is very stable and the benzoyl peroxide remains in solution, i.e., an analysis of the cosmetic solution does not show any crystalline benzoyl peroxide. Further, primary irritation tests indicate this solution to be minimally irritating which is important for its use as a vehicle for topical application.

3 Claims, No Drawings

4,925,666

SOLUBILIZED BENZOYL PEROXIDE AND COSMETIC SOLUTION INCLUDING SOLUBILIZED BENZOYL PEROXIDE

This is a continuation of application Ser. No. 016,839, filed Feb. 20, 1987, now U.S. Pat. No. 4,857,302.

BACKGROUND OF THE INVENTION

The present invention relates to a solubilized form of benzoyl peroxide and a method of manufacturing the solubilized benzoyl peroxide base solution. The invention also relates to a cosmetic solution which utilizes the solubilized benzoyl peroxide base as well as a method of manufacturing the cosmetic solution.

For almost 70 years, Benzoyl peroxide has been used as a keralolytic and antibacterial agent in the topical treatment of various skin conditions such as seborrhea and acne vulgaris. Basically, benzoyl peroxide dries the upper or outer layers of skin and causes that dried skin to sluff off. Benzoyl peroxide has a general chemical formula of $(C_6 H_5 CO)_2 O_2$. Benzoyl peroxide is a non-toxic, colorless, odorless, and tasteless crystalline solid with a molecular weight of 242.22 and a melting point of between 103° to 106° C. It is known that benzoyl peroxide is sparingly soluble in $H_2O$ or alcohol and is soluble in benzene, chloroform and ether. Other uses of benzoyl peroxide include use as an oxidizer in bleaching oils, flour, etc., as a catalyst in the plastics industry and as an initiator in polymerization. Commonly, benzoyl peroxide is available in a hydrous form (wet form) as a crystal. The water in the granules of hydrous benzoyl peroxide is utilized to reduce flammability and shock sensitivity.

Various commercially available products containing benzoyl peroxide for the treatment of skin conditions are available on the over the counter market from companies such as Norcliff Thayer of Tarrytown, N.Y., Westwood Pharmaceuticals of Buffalo, N.Y., and Richardson-Vicks of Wilton, Conn. In these commercially available, over-the-counter products utilized by consumers, the concentration of benzoyl peroxide is up to 10% benzoyl peroxide by weight. The 10% maximum is approved for over-the-counter preparations by the Federal Food and Drug Administration.

Prior to the present invention, the only way to deliver benzoyl peroxide for topical use has been in suspension form where finely ground particles of benzoyl peroxide are disbursed and suspended in various lotions, creams or gel bases. These preparations are available to the general public as an over-the-counter product or available in higher benzoyl peroxide strengths by prescription from a physician. Although benzoyl peroxide is soluble in some industrial solvents, such as aromatic solvents including toluene and methel-ethyl keytone, these industrial solvents are highly flamable and are irritant for human use. Therefore, the preparations are unusable in the over-the-counter drug market or the prescription markets. The exception is the use of acetone to place the benzoyl peroxide in solution.

Acetone is used to a limited degree in some topical formulations. The use of acetone is greatly limited by the fact that acetone is a primary irritant, extremely drying and presents a severe fire hazard, i.e., is flammable. Tests have shown that over-the-counter preparations use crystallized or insoluble benzoyl peroxide notwithstanding the presence of acetone. Therefore prior to this invention, existing benzoyl peroxide products utilized benzoyl peroxide in crystalline form and the crystals were suspended in a liquid or gel.

One known, prior art product by Richardson-Vicks, Inc., sold under the trade name Clearasil, includes benzoyl peroxide at 10% concentration as an active ingredient along with the following ingredients: water, aluminum hydroxide, isopropyl stearate, PEG-100 stearate, glyceryl stearate, cetyl alcohol, glycereth-26, isocetyl stearate, glycerin, dimethicone copolyol, sodium citrate, citric acid, methylparaben, propylparaben, and fragrance. An examination under a 40X power (objective power) microscope of this product revealed that the benzoyl peroxide is still in crystalline form and hence is not solubilized within the lotion.

OBJECTS OF THE PRESENT INVENTION

It is an object of the present invention to provide a solubilized form of benzoyl peroxide.

It is another object of the present invention to provide a solution of benzoyl peroxide and silicone glycol copolymer.

It is another object of the present invention to provide a benzoyl peroxide solution wherein the crystals of benzoyl peroxide are substantially dissolved within silicone glycol copolymer.

It is a further object of the present invention to provide a benzoyl peroxide solution that has a long shelf life and that remains stable notwithstanding significant changes in temperature.

It is another object of the present invention to provide a benzoyl peroxide solution that is colorless, substantially odorless and that has benzoyl peroxide an active ingredient as in solution.

It is an object of the present invention to provide a cosmetic solution that includes solubilized benzoyl peroxide.

It is another object of the present invention to provide a cosmetic solution having solubilized benzoyl peroxide that has a long shelf life.

It is an additional object of the present invention to provide a cosmetic solution with active benzoyl peroxide wherein the benzoyl peroxide is not substantially crystalline, i.e., has benzoyl peroxide in solution.

It is a further object of the present invention to provide a cosmetic solution which maintains its stability over a long time and over a wide temperature range.

It is a further object of the present invention to provide a cosmetic solution which is clear, essentially colorless, and has a relatively stable pH.

It is a further object of the present invention to provide a cosmetic solution to which, after preparation, certain cosmetically approved materials and/or compositions can be added to the original cosmetic solution to enhance the cosmetic attributes of the overall solution without causing the benzoyl peroxide to crystallize and precipitate from the cosmetic solution.

SUMMARY OF THE INVENTION

The solubilized benzoyl peroxide is made by mixing a heated combination of crystalline benzoyl peroxide, that customarily includes some water to reduce the flammability of the benzoyl peroxide and the shock sensitivity, with silicone glycol copolymer wherein the temperature of the mixture is in the range from approximately 45° to 65° C. An analysis of the resulting solution reveals that the benzoyl peroxide is no longer in crystallized form and hence the benzoyl peroxide is solubilized within the silicone glycol copolymer.

The cosmetic solution that includes solubilized benzoyl peroxide utilizes the solubilized benzoyl peroxide as described above. Further, an independent mixture of alcohol, acetone and water is made. The solubilized benzoyl peroxide, the benzoyl peroxide and silicone glycol copolymer, is mixed with the second mixture (alcohol, acetone and water) to obtain the cosmetic solution. The resulting cosmetic solution is very stable and the benzoyl peroxide remains in solution, i.e., analysis of the cosmetic solution does not show any crystalline benzoyl peroxide.

Further objects and advantages of the present invention are found in the accompanying detailed description of the preferred embodiments.

DETAILED DESCRIPTION OF THE PREFERRED EMBODIMENTS

The present invention relates to a solubilized form of benzoyl peroxide as well as related to a new cosmetic solution that includes the solubilized benzoyl peroxide.

The solubilized benzoyl peroxide solution is sometimes referred to in this description as a base solution since the solubilized form of benzoyl peroxide is utilized in the cosmetic solution that is described later in detail.

The solubilized form of benzoyl peroxide is made by mixing a heated combination of benzoyl peroxide with silicone glycol copolymer. Silicone glycol copolymer is called dimethicone copolyol by the Cosmetic Toiletry and Fragrance Association (CTFA).

Benzoyl peroxide has a crystalline form and is commercially sold in a granular wet form that includes water in order to reduce the flammability of the benzoyl peroxide granules and to provide for shock sensitivity. Customarily, this is called hydrous benzoyl peroxide. Commercially availably hydrous benzoyl peroxide can reach 98% benzoyl peroxide, however, this high concentration of benzoyl peroxide is extremely flammable and therefore dangerous to use. It is known that 70% benzoyl peroxide is available from US Peroxygen, Witco Chemical Corporation of Richmond, Calif. and is sold under the tradename BZW-70. The specific examples discussed later identify this type of benzoyl peroxide by its tradename, BZW-70. Due to the relative similarity between all of the forms of benzoyl peroxide, BZW-70 is representative of the characteristics of benzoyl peroxide in general.

Benzoyl peroxide has a general chemical formula as follows:

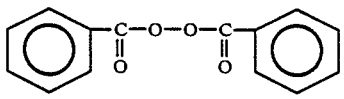

It was discovered that mixing a heated combination of benzoyl peroxide and silicone glycol copolymer produces a solubilized form of benzoyl peroxide. Various temperatures were utilized during this mixing. At temperatures exceeding approximately 65° C., the mixture begins to profusively foam due principally to uncontrolled oxidation and the release of oxygen. The pH of the solution drops. However, after the foaming solution is cooled and the solution returns to its generally liquid state, testing of the solution reveals that the benzoyl peroxide is still solubilized within the silicone glycol copolymer. Preferably, the temperature at which the benzoyl peroxide and silicone glycol copolymer mixture is mixed, is in the range between approximately 45° to 65° C. Optimally, the temperature range is between approximately 55-60° C. The mixing can be done by a magnetic stirrer or a mechanical mixer. One experiment revealed that the time for mixing is between 30 minutes to 1 hour. Another experiment showed that the silicone glycol copolymer can be heated separately and the crystalline benzoyl peroxide added subsequent thereto.

The temperature at which the mixture is heated and the amount of time necessary to completely dissolve the benzoyl peroxide varies dependent upon the concentration of benzoyl peroxide crystals in the silicone glycol copolymer. After the benzoyl peroxide is dissolved, the solution clears since a mixture of benzoyl peroxide and silicone glycol copolymer prior to solution is milky in color. Experiments have shown that by adding acetone to the initial mixture of benzoyl peroxide and silicone glycol copolymer, the temperature required to solubilize the benzoyl peroxide is reduced and also the time of mixing is reduced.

It has been confirmed that the benzoyl peroxide is solubilized in the silicone glycol copolymer because microscopic analysis of the resulting solution under low, medium, and high power of the microscopes (400X magnification at high power) reveals that no crystalline benzoyl peroxide is present.

Further, a standard active oxygen analysis of the solubilized benzoyl peroxide, an accepted wet analytic technique confirms the presence of active benzoyl peroxide in the solubilized base solution. In one experiment, the silicone glycol copolymer is manufactured by Dow Corning Corporation of Midland, Mich., and is sold under the tradename Dow Corning 190 and 193 fluid. Specifically, experiments were carried out using silicone glycol copolymer Dow Corning 190 fluid. The general chemical formula of silicone glycol copolymer is as follows:

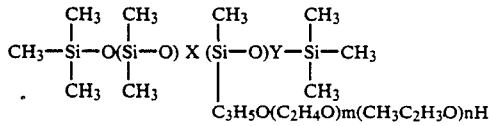

Silicone glycol copolymer is available commercially in different grades offered by several different companies. Dow Corning 190 fluid is a different grade of the copolymer as compared with Dow Corning 193 fluid. The differences between the grades of silicone glycol copolymer is determined by the X, Y, m and/or n in the general chemical formula. The specific grades of silicone glycol copolymer and the number of repeating units of X, Y, m, n are maintained as trade secrets by these companies. However, further experiments using different grades of silicone glycol copolymer have confirmed that the general solubility of the benzoyl peroxide is not affected by the different grades but rather the percentage by weight of benzoyl peroxide that can be placed in solution is affected. An experiment mixing 190 fluid and BZW-70 at room temperature (about 25° C.) for about eight hours revealed that the benzoyl peroxide was not soluable in the silicone glycol copolymer.

The stability of the solubilized benzoyl peroxide base solution is an unexpected result. Experimental tests have confirmed that the benzoyl peroxide stays in solution even though the solution undergoes several freeze/thaw cycles and the benzoyl peroxide remains in solution for an undetermined amount of time. The benzoyl peroxide base solution was cooled to below about 0° C. and rewarmed three times by placing the solution in a freezer and raising the temperature of the base solution to room temperature at least three repetitive times. Also, an accelerated shelf life stability test was conducted on the solubilized benzoyl peroxide base solution. The solution was heated to approximately 35° C. for approximately seven months. In both the freeze/thaw cycling test and the accelerated shelf life stability test, no precipitation or recrystallization of the benzoyl peroxide was noted in the tested base solutions.

Further, the color or the clarity of the benzoyl peroxide base solution did not change during these tests. The color test involved comparing a fresh benzoyl peroxide base solution to the solution that underwent the freeze/thaw cycling test and, independently, the accelerated shelf life stability test. Further, the tested base solutions were tested for pH changes. It is well known that when benzoyl peroxide breaks down, the resulting solution is yellowish to brownish color and the pH of the solution changes.

The presence of active benzoyl peroxide in the base solution was also confirmed by adding water ($H_2O$) to the base solution. Immediately upon the addition of water, the benzoyl peroxide precipitates out as noted by an immediate color change of the solution.

Experiments utilizing benzoyl peroxide BZW-70 and silicone glycol copolymer Dow Corning 190 fluid indicate that the maximum percentage, by weight, of BZW-70 to the 190 fluid is 23.33% BZW-70 to 76.67% Dow Corning 190 fluid. Since the BZW-70 is 30% water by weight, given these specific elements, it seems the maximum amount of benzoyl peroxide that can be solubilized in the specific silicone glycol copolymer Dow Corning 190 fluid is approximately 16% benzoyl peroxide, by weight. However, different grades of silicone glycol copolymer may raise this maximum percentage of benzoyl peroxide that is soluble.

Based upon this information, and particularly based upon the stability of the benzoyl peroxide base solution, it is believed that some type of steric relationship may exist between the silicone glycol copolymer and the benzoyl peroxide. Since the grades of silicone glycol copolymer relate to the length of the silicone chain and/or the carbon side chains and particularly the number of repeating units X, Y, m, n, and different maximum amounts of benzoyl peroxide can be soluble in different grades of silicone glycol copolymer, and the stability of the base solution is very high, it seems that the benzoyl peroxide molecule may, in some manner, be affected by and linked to the repeating units in the silicone glycol copolymer.

In any event, since the benzoyl peroxide is in solution, is highly stable, and is in a relatively high concentration, the soluble form of benzoyl peroxide is very useful in many applications and particularly in the cosmetic industry.

The desired concentration of the benzoyl peroxide in the base solution may be determined by what concentration of benzoyl peroxide is desired in the finished cosmetic product sold to the general public. Further, the concentration of benzoyl peroxide in the base solution is principally determined by what type of aesthetic qualities the finished cosmetic product must possess. Also, since the silicone glycol copolymer affects the viscosity of the base solution, that viscosity must be taken into account when formulating a cosmetic solution utilizing the solubilized benzoyl peroxide base solution. In general, a person would calculate the necessary percentage of benzoyl peroxide backwards, starting from the desired percentage in the final cosmetic solution to obtain the proper benzoyl peroxide percentage in the base solution. For example, since over-the-counter products may only include up to 10% benzoyl peroxide, the concentration of benzoyl peroxide in the base solution is very dependent upon the amount of other components in the cosmetic end product.

Based upon the testing of the benzoyl peroxide base solution, particularly, the color testing and pH testing, it is clear that benzoyl peroxide is still an active agent in the base solution. Further testing has been conducted on other surfactants other than silicone glycol copolymer and the benzoyl peroxide does not seem to be soluble in those other surfactants.

The present invention also relates to a cosmetic solution which utilizes the solubilized benzoyl peroxide base solution. Since benzoyl peroxide has not been solubilized, except in certain organic solvents, prior to the present invention, and due to certain attributes of the benzoyl peroxide base solution, the cosmetic solution that incorporates several other components is a significant advance.

The cosmetic solution is utilized particularly to treat skin conditions as noted above in the discussion of the background of the invention. Generally, the cosmetic solution involves preparing a benzoyl peroxide base solution, separately preparing a second mixture of various cosmetically effective and acceptable components, and then mixing the benzoyl peroxide base solution with the second mixture.

The second mixture generally includes alcohol, acetone and water. Particularly, one experiment utilized isopropyl alcohol, acetone and deionized water. This second mixture is mixed with the benzoyl peroxide base solution. The benzoyl peroxide did not precipitate or become desolubilized during this preparation.

In contrast, if anhydrous alcohol is added to the benzoyl peroxide base solution independently, the benzoyl peroxide precipitates out of the resulting liquid. When acetone was added to the benzoyl peroxide base solution independent of the alcohol and water, the benzoyl peroxide did not precipitate out. However, the subsequent addition of alcohol or the subsequent addition of water did cause the benzoyl peroxide in the liquid to precipitate out. Another experiment showed that the addition of water to the benzoyl peroxide base solution caused the precipitation of the benzoyl peroxide. Therefore, it is important to independently mix or prepare the benzoyl peroxide base solution, independently prepare the alcohol, acetone and water solution, and then mix the two solutions together in order to preserve the solubility of the benzoyl peroxide in final cosmetic solution. This is an unexpected result.

Ideally, experiments have shown that equal parts of anhydrous isopropyl alcohol and/or ethanol 190 proof, acetone and water provide for a stable, cosmetic solution having 5% by weight benzoyl peroxide. This solution underwent the freeze/thaw cycling test, the pH test, the color test and the microscopic analysis described above with respect to the benzoyl peroxide base solution. The benzoyl peroxide remained in the solution throughout these test.

After preparation of this cosmetic solution, additional components can be added to the cosmetic solution to enhance the commercial, aesthetic, physical, and cosmetic attributes of the solution. For example, it is found that further additives such as glycerine, or eucalyptol enhance the ultimate finished cosmetic product.

Tests have shown that the alcohol can be either ethyl, isopropyl, or benzyl. Butanol and/or other fatty alcohols may be compatible with the base solution but in lower amounts than the ethyl and/or isopropyl alcohols.

The ratio between the alcohol, acetone and water varies dependent upon the final benzoyl peroxide concentration or the cosmetic properties desired for the final cosmetic solution. Generally, experiments have shown that the greater the percentage of benzoyl peroxide, the greater percentage of acetone required. In turn, the greater the amount of acetone, the lower the amount of silicone glycol copolymer required. Of course, since a cosmetic product is produced by this procedure, and since acetone is highly flammable and irritating, minimizing the amount of acetone is important. Likewise, the lower the percentage by weight of benzoyl peroxide, the higher the percentage of water that can be placed in the cosmetic solution. For example, tests have shown that a 5% benzoyl peroxide cosmetic solution will tolerate approximately 22% water while maintaining the solubility of the benzoyl peroxide. Likewise, a 10% benzoyl peroxide cosmetic solution will tolerate approximately 10% water.

One finished cosmetic solution possessing excellent clarity and tactile properties during topical application, includes the following chemical ingredients:

TABLE I

| 5%, by weight, of Benzoyl Peroxide | |
|---|---|
| Silicone glycol copolymer (Dow Corning 190 Fluid) | 23.0% |
| BZW-70 | 7.0% |
| Isopropyl Alcohol | 21.9% |

TABLE I-continued

| 5%, by weight, of Benzoyl Peroxide | |
|---|---|
| Acetone | 21.9% |
| $H_2O$ | 21.9% |
| Glycerine | 3.0% |
| Eucalyptol | 1.3% |

For a 2% cosmetic solution of benzoyl peroxide, acetone in the range of 16–22%, water in the range of 32–26% respectively and isopropyl alcohol at 22% resulted in a stable solution that maintained the solubility of the benzoyl peroxide.

Further additives may be included in the cosmetic solution without disturbing the solubility of the benzoyl peroxide. For example, propylene glycol is a candidate for these additions.

The claims appended hereto are meant to cover changes and modifications within the scope and spirit of the invention.

What we claim is:

1. A method for preparing a cosmetic composition with benzoyl peroxide, comprising the steps of:
   preparing a mixture comprising between about 2% and about 16%, by weight, benzoyl peroxide and between 23% and about 98%, by weight, silicone glycol copolymer; and
   heating said mixture to between about 35° and about 65° centigrade to obtain solubilized benzoyl peroxide in the silicone glycol copolymer.

2. The method of claim 1, wherein said mixture is a first mixture and further comprising the step of mixing with said first mixture a second mixture comprising alcohol, acetone, and water.

3. The method of claim 2, further comprising the step of cooling said first mixture prior to combination with said second mixture.

* * * * *